United States Patent [19]

Yamamoto et al.

[11] Patent Number: 5,101,070

[45] Date of Patent: Mar. 31, 1992

[54] PROCESS FOR PREPARING VALPROIC ACID

[75] Inventors: Toshio Yamamoto, Suita; Akira Yamashita, Omihachiman; Noriyoshi Numoto, Toyonaka, all of Japan

[73] Assignee: Nippon Gohsei Kagaku Kogyo Kabushiki Kaisha, Osaka, Japan

[21] Appl. No.: 215,276

[22] Filed: Jul. 5, 1988

Related U.S. Application Data

[63] Continuation of Ser. No. 924,733, Oct. 30, 1986, abandoned.

[51] Int. Cl.$^5$ ............... C07C 27/02; C07C 51/09; C07C 53/126
[52] U.S. Cl. ................... 562/606; 560/174; 560/265
[58] Field of Search .............. 562/606; 560/174, 265

[56] References Cited

U.S. PATENT DOCUMENTS 4,127,604 11/1978 Chignac et al. .......... 562/606
4,317,925 3/1982 Weber et al. .......... 562/606 X

FOREIGN PATENT DOCUMENTS 112320 2/1974 Japan .............. 560/174
156638 8/1985 Japan .............. 562/606

Primary Examiner—Vivian Garner
Attorney, Agent, or Firm—Antonelli, Terry Stout & Kraus

[57] ABSTRACT

A process for preparing valproic acid which comprises:
(I) producing a 2,2-dipropyl acetoacetic acid ester from an acetoacetic acid ester,
(II) deacetylating the 2,2-dipropyl acetoacetic acid ester with an alcohol to give a valproic acid ester, and
(III) hydrolyzing the valproic acid ester. In the process of the present invention, valproic acid can be prepared in a high yield as not less than 85% by mole and by-products such as α-propyl-β-ethyl acrylic acid and its esters which cannot be easily separated from valproic acid, are not entirely produced.

9 Claims, No Drawings

PROCESS FOR PREPARING VALPROIC ACID

This is a continuation of application Ser. No. 924,733, filed Oct. 30, 1986, now abandoned.

BACKGROUND OF THE INVENTION

The present invention relates to a process for preparing valproic acid useful for various uses including medicines.

As a process for preparing valproic acid, there have hitherto been known (a) a process using 4-hydroxy-heptane as a starting material, (b) a process using cyanoacetic acid ester as a starting material, (c) a process using a malonic acid ester as a starting material, and the like. However, the above-mentioned processes are unsatisfactory in industrial scale since the yields of valproic acid are about 70% by mole in all the processes (a) to (c). Moreover, in the process (a), reagents such as Grignard reagent and sodium prussiate, which are expensive and must be handled carefully, must be employed, in the process (b), the reaction conditions are very severe, and in the process (c), expensive starting materials are required.

Japanese Unexamined Patent Publication (Tokkyo Kokai) No. 156638/1985, as an improved process of the above-mentioned processes (a) to (c), has disclosed a process for preparing valproic acid which comprises:

(1) reacting an acetoacetic acid ester with an allyl halide to give a 2,2-diallyl acetoacetic acid ester, (2) reacting an alcohol with the 2,2-diallyl acetoacetic acid ester to give a diallyl acetic acid ester, and (3) hydrolyzing the diallyl acetic acid ester to give a diallyl acetic acid and reducing the diallyl acetic acid, or (3)' reducing the diallyl acetic acid ester to give a valproic acid ester and hydrolyzing the valproic acid ester.

The process disclosed in Tokkyo Kokai No. 156638/1985 has an advantage that valproic acid can be easily produced from cheap starting materials, but in the step (3) or (3)', an $\alpha$-propyl-$\beta$-ethyl-acrylic ester is produced as a by-product. Although the amount of the by-product is small, the by-product remarkably lowers the quality as medicines since it cannot be easily removed with usual purifications. Accordingly, valproic acid obtained by the abovementioned process requires an additive step for removing the by-product.

An object of the present invention is to provide an industrially excellent process for preparing valproic acid improving the above-mentioned disadvantage.

The above and other objects of the present invention will become apparent from the description hereinafter.

SUMMARY OF THE INVENTION

In accordance with the present invention, there is provided a process for preparing valproic acid which comprises:

(I) producing a 2,2-dipropyl acetoacetic acid ester from an acetoacetic acid ester, (II) deacetylating the 2,2-dipropyl acetoacetic acid ester with an alcohol to give a valproic acid ester, and (III) hydrolyzing the valproic acid ester.

DETAILED DESCRIPTION

Step (I)

In the present invention, as the first step, a 2,2-dipropyl acetoacetic acid ester is prepared. For preparing the 2,2-dipropyl acetoacetic acid ester, there are two methods as follows:

(1)(a) A 2,2-diallyl acetoacetic acid ester is prepared by reacting an acetoacetic acid ester with an allyl halide.

$$CH_3CO-CH_2-COOR + 2CH_2=CH-CH_2-X \longrightarrow$$

$$\begin{matrix} & CH_2-CH=CH_2 \\ & | \\ CH_3CO-C-COOR & + 2HX \\ & | \\ & CH_2-CH=CH_2 \end{matrix}$$

wherein R is an alkyl group having 1 to 6 carbon atoms and X is a halogen atom

Examples of the preferable alkyl acetoacetate are, for instance, methyl acetoacetate, ethyl acetoacetate, and the like.

Examples of the preferable allyl halides are, for instance, allyl bromide, allyl chloride, and the like.

The reaction of the acetoacetic acid ester and the allyl halide is carried out generally in the presence of a catalyst, preferably in the presence of the basic catalyst and a phase-transfer catalyst.

Examples of the phase-transfer catalyst are, for instance, quaternary ammonium salt such as benzyltrimethylammonium chloride, benzyltrimethylammonium bromide, benzyltriethylammonium chloride, benzyltriethylammonium bromide, tetramethylammonium chloride, tetramethylammonium bromide, tetraethylammonium chloride, tetraethylammonium bromide, tetrapropylammonium chloride, tetrapropylammonium bromide, tetrabutylammonium chloride, tetrabutylammonium bromide, dodecyltrimethylammonium chloride, dodecyltrimethylammonium bromide, dodecyltriethylammonium chloride, dodecyltriethylammonium bromide, cetyltrimethylammonium chloride, cetyltrimethylammonium bromide, cetyltriethylammonium chloride, cetyltriethylammonium bromide, and the like.

Examples of the basic catalysts are, for instance, a hydroxide of alkali metal such as sodium hydroxide or potassium hydroxide, a carbonate of alkali metal such as sodium carbonate or potassium carbonate, an alcoholate of alkali metal such as sodium alcoholate or potassium alcoholate, a hydroxide of alkaline earth metal such as calcium hydroxide, a carbonate of alkaline earth metal such as calcium carbonate, and the like. The combination of tetrabutylammonium chloride or bromide and the hydroxide of alkali metal (aqueous solution) is the most effective because valproic acid can be prepared in high yields and these catalysts can be easily available and handled.

A solvent may be employed or not. Examples of the solvents are, for instance, toluene, benzene, xylene, acetonitrile, dimethyl formamide, dimethyl sulfoxide, and the like.

The amount of the allyl halide is from 2 to 50 moles per mole of the acetoacetic acid ester.

The basic catalyst in used in the amount of more than 2 moles, preferably from 2 to 3 moles, per mole of the acetoacetic acid ester.

The phase-transfer catalyst is employed in an amount of not less than 0.01 mole, preferably from 0.05 to 0.5 mole, per mole of the acetoacetic acid ester.

The mole ratio of the phase-transfer catalyst to the basic catalyst is preferably selected from 0.01 to 0.5.

It is practical to use the solvent in an amount of less than 50 times the weight of the acetoacetic acid ester.

These chemical agents can be charged in any manners, for example, supplied at once, intermittently or continuously.

The reaction temperature is from 0° C. to a boiling point of solvent or allyl halide, preferably from 10° C. to 40° C. The reaction time is from 2 to 24 hours.

After completing the reaction, the reaction mixture is cooled. Then, the undissolved components are filtered off from the reaction mixture and the filtrate is concentrated to give a desired product. As occasion demands water is added to the reaction mixture, the separated organic layer is concentrated to give a desired product. The obtained product is, if necessary, purified.

The yield of the obtained 2,2-diallyl acetoacetic acid ester is high, i.e. not less than 90% by mole to the acetoacetic acid ester.

(1) (b) Secondarily, a 2,2-dipropyl acetoacetic acid ester is prepared by reducing the 2,2-diallyl acetoacetic acid ester.

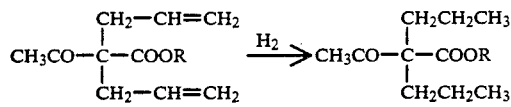

wherein R is as defined above.

Any reducing methods such as catalytic hydrogenation and reduction using reducing agents are applicable to reducing the 2,2-diallyl acetoacetic acid ester, and the catalytic hydrogenation is industrially preferable.

In the catalytic hydrogenation, a solvent may be employed or not. Examples of the employed solvents are, for instance, a lower alcohol having 1 to 6 carbon atoms such as methanol, a lower fatty acid having 1 to 5 carbon atoms such as acetic acid, propionic acid or butyric acid, and the like. Among them, methanol and acetic acid are preferably employed. The above-mentioned solvents may contain a small amount of water. The amount of the solvent is at least twice times, preferably from 3 to 20 times the weight of the 2,2-diallyl acetoacetic acid ester.

As the catalyst, a nickel catalyst such as Raney nickel catalyst is most preferably used, and a palladium catalyst such as palladium-on-carbon and a platinum catalyst can be also used. The amount of the catalyst is not less than 0.5% by weight, preferably from 1% to 6% by weight based on the 2,2-diallyl acetoacetic acid ester.

The reduction reaction can be carried out at atmospheric pressure or under pressure. The reaction temperature depends on kinds of solvents. Generally, the temperature is from room temperature to 200° C., and preferably from 40° C. to 60° C. The end point of the reaction is the time when the absorption of hydrogen gas stops, and generally, the reaction time is from 1 to 10 hours.

The 2,2-diallyl acetoacetic acid ester can be reduced by using a reducing agent such as lithium/ammonia, hydrogenated tri-phenyl tin.

The yield of the 2,2-dipropyl acetoacetic acid ester to the 2,2-diallyl acetoacetic acid ester is nearly 100% by mole and a by-product is not at all produced.

(2) In step (I), the 2,2-dipropyl acetoacetic acid ester can be prepared by reacting the acetoacetic acid ester with a propyl halide instead of the allyl halide.

wherein R and X are as defined above.

The reaction of the propyl halide and the acetoacetic acid ester can be substantially carried out in the same manner as shown in the step (I) (1). That is, the acetoacetic acid ester and the propyl halide are reacted in the presence of the basic catalyst and the phase-transfer catalyst at a temperature of about 0° C. to about 90° C. for several hours. After completing the reaction, the organic layer are separated from the reaction mixture and a desired product is obtained from the organic layer.

Step (II)

In the present invention, as the second step, a valproic acid ester is prepared by deacetylating the 2,2-dipropyl acetoacetic acid ester with an alcohol.

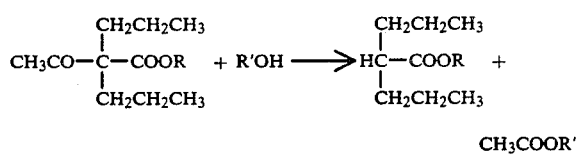

wherein R is as defined above and R' is an alkyl group.

As an alcohol used in the step (II), there are used alcohols having 1 to 6 carbon atoms, such as methanol, ethanol, propanol, butanol and hexanol. In the step (II), the alcohol functions as a solvent as well as it reacts with the 2,2-dipropyl acetoacetic acid ester, and accordingly, in the step (II), it is not necessary to employ other solvents in addition to the alcohols.

The same basic catalyst as used in the step (I) can be used in the step (II). Among them, the sodium alcoholate and the potassium alcoholate are preferable. The amount of the catalyst is not less than 0.01 mole, preferably from 0.05 to 1.0 mole per mole of the 2,2-dipropyl acetoacetic acid ester.

The amount of the alcohol is from 1 to 50 moles per mole of the 2,2-dipropyl acetoacetic ester.

In the step (II), the chemical agents used can be charged in any manners as in the step (I). The reaction time is from 0.5 to 10 hours and the reaction temperature is from 50° C. to a reflux point.

The yield of the valproic acid ester to the 2,2-dipropyl acetoacetic acid ester is not less than 95% by mole.

Step (III)

In the present invention, as the third step, valproic acid is prepared by hydrolyzing the valproic acid ester.

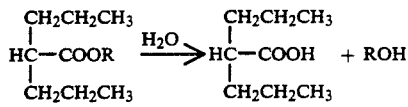

wherein R is as defined above.

After concentrating the product obtained in the step (II), the valproic acid ester is hydrolyzed by heating under reflux at a temperature of 50°0 C. to 100° C. for about 2 to about 5 hours. Then, the pH of the reaction solution is adjusted to 9 to 10 and the solution is extracted with toluene, benzene, and the like. After adjusting the pH of the aqueous layer to about 2, it is allowed to stand to separate an organic layer containing the valproic acid. The valproic acid is obtained from the organic layer. The obtained valproic acid may be, if necessary, purified.

As aforementioned, in the present invention, it is possible to prevent the production of the by-products which cannot be easily separated from valproic acid, and accordingly the process of the present invention is industrially very advantageous since an additive step for removing the by-product is not required. Also, the yield of the valproic acid to the acetoacetic acid ester used as the starting material is high, i.e. not less than 85% by mole.

The present invention is more specifically described and explained by means of the following Examples in which all parts and % are by weight unless otherwise noted. It is to be understood that the present invention is not limited to the Examples, and various changes and departing from the spirit and scope thereof.

EXAMPLE 1

Preparation of methyl 2,2-diallyl acetoacetate: Step (I) (1) (a)

A reactor equipped with a condenser and a stirrer was charged with 64.4 g of tetrabutylammonium bromide, 140 g of 40% aqueous solution of sodium hydroxide and 1530 g of allyl chloride and the mixture was stirred. The reaction was carried out by adding dropwise 232.2 g of methyl acetoacetate to the mixture at 20° C. to 30° C. for 3 hours. During the reaction, each 140 g portion of the same aqueous solution of sodium hydroxide as shown above was additionally added to the reactor after 50 minutes and after 110 minutes from the beginning of addition of methyl acetoacetate. After charging the total amounts, the stirring was continued for 1.5 hours and 100 g of water was added to the reaction mixture. The separated organic layer was concentrated to give 440 g of a yellow liquid.

The obtained concentrate was washed with water and the organic layer was distilled under reduced pressure to give 372.5 g of a main fraction (from 74° C./2.5 mmHg to 76° C./2.3 mmHg).

Tetrabutyl ammonium salt was recovered from the aqueous layer by concentrating the aqueous layer in a recovery of 95%.

As a result of the quantitative analysis of the main fraction by gas chromatography, it was confirmed that the content of methyl 2,2-diallyl acetoacetate was 97%, and its yield to methyl acetoacetate was 92% by mole.

Preparation of methyl 2,2-di-n-propyl acetoacetate: Step (I) (1) (b)

An autoclave was charged with 372.5 g of the main fraction having methyl 2,2-diallyl acetoacetate as a main component obtained in the step (I) (1) (a), 15 g of Raney nickel (water content: 50%) and 800 g of methyl alcohol and the atmosphere in the autoclave was displaced with hydrogen gas. The reduction was carried out at 50° C. to 57° C. under a hydrogen pressure of 1.1 kg/cm$^2$ with stirring. The stirring was continued for 30 minutes after the time when the absorption of hydrogen gas was completed, that is, for about 5 hours, to complete the reduction reaction. After filtering off the catalyst and then removing methanol from the filtrate, the resultant was distilled under reduced pressure to give 361.2 g of a main fraction (from 73° C./1 mmHg to 77° C./2.5 mmHg).

As a result of the analysis of the main fraction by gas chromatography, it was confirmed that the conversion of methyl 2,2-diallyl acetoacetate is 100%, the yield of methyl 2,2-dipropyl acetoacetate to methyl 2,2-diallyl acetoacetate is 97% by mole and other reduction products were not prepared.

Preparation of methyl valproate: Step (II)

A reactor equipped with a condenser and a stirrer was charged with 142.2 g of methyl 2,2-dipropyl acetoacetate, 15.1 g of 28% methanol solution of sodium methylate and 22 g of methanol and the reaction was carried out for 2.5 hours under reflux.

After removing methyl acetate produced at the reaction for 2 hours from the reaction mixture, the concentration was conducted at atmospheric pressure to give 123.5 g of a dark brown concentrate.

As a result of the analysis of the concentrate by gas chromatography, it was confirmed that the content of methyl valproate was 87% and its yield to methyl 2,2-dipropyl acetoacetate was 98% by mole.

Preparation of valproic acid: Step (III)

There were added 106 g of 40% aqueous solution of sodium hydroxide and 44 g of water to the concentrate obtained in the step (II), the mixture was reacted at 71° C. to 88° C. for 2 hours and the reaction mixture was concentrated at atmospheric pressure.

To the obtained concentrate was added 130 ml of water, which was washed twice time with toluene in an equal amount of the total amount of the concentrate and water. After separating, 194 g of 30% aqueous solution of sulfuric acid was added to the obtained aqueous layer, and the produced oil layer was taken out. To the obtained oil layer was added 10 g of magnesium sulfate, and the mixture was thoroughly stirred and filtered to give 105 g of a filtrate.

As a result of the analysis of the filtrate by gas chromatography, it was confirmed that the content of valproic acid was 92.6% and its yield to methyl valproate was 97% by mole.

A fraction of 87° C./3 mmHg was collected by rectification of the obtained filtrate to give valproic acid having a purity of 99.9%. Also, α-propyl-β-ethyl-acrylic acid and its esters were not included in the obtained product.

Examples 2 to 4

The procedure of Example 1 was repeated except that conditions of the steps (I) to (III) were changed to those shown in Table 1 to prepare valproic acid.

In the steps (I) to (III), by-products which cannot be easily separated from valproic acid were not entirely produced.

The results are shown in Table 1.

TABLE 1

| Starting material Kind (Amount) | Step (I) (1) (a) | Step (I) (1) (b) | Step (II) | Step (III) | Yield[3] (% by mole) |
|---|---|---|---|---|---|
| Ex. 2 AAM[1] (2 moles) Allyl chloride (20 moles) | Catalyst: Benzyl-triethylammonium bormide 91.2 g Solvent: Benzene 700 ml | According to Example 1 | According to Example 1 | According to Example 1 | 85% |
| Ex. 3 AAM[1] (2 moles) Allyl bromide (20 moles) | | Hydrogen pressure: 1.1 kg/cm² Catalyst: 5% Palladium-on-carbon 15 g | In ethanol solution of sodium ethylate | According to Example 1 | 86% |
| Ex. 4 AAE[2] (2 moles) Allyl chloride (20 moles) | According to Example 1 | According to Example 1 | In ethanol solution of sodium ethylate | According to Example 1 | 85% |

(Notes)
AAM[1]: Methyl acetoacetate
AAE[2]: Ethyl acetoacetate
Yield[3]: A yield of valproic acid to the acetoacetic acid ester

Example 5

A reactor was charged with 123 g (1 mole) of n-propyl bromide, 32.3 g (0.1 mole) of tetrabutylammonium bromide and 114 g of 35% aqueous solution of sodium hydroxide, and 58.1 g (0.5 mole) of methyl acetoacetate was added dropwise to the mixture at about 70° C. for 1 hour with stirring. The reaction was continued at 75° C. to 85° C. for 3 hours and the reaction mixture was cooled. To the reaction mixture was added 100 g of water and it was separated into an oil layer and an aqueous layer. The oil layer (about 133 g) was concentrated, from which unreacted components was removed and the distillation was conducted to give methyl 2,2-dipropyl acetoacetate.

Valproic acid was prepared from the obtained methyl 2,2-dipropyl acetoacetate in the same manner as in Example 1.

The yield of valproic acid to methyl acetoacetate was 85% by mole. Also the obtained product did not entirely include by-products such as α-propyl-β-ethyl-acrylic acid or its ester.

Example 6

Step (I) (1) (a)

A reactor equipped with a condenser and a stirrer was charged with 11.6 g of methyl acetoacetate, 100 ml of dimethyl formamide, 23.0 g of allyl chloride and 29.0 g of potassium carbonate and the mixture was reacted with stirring at 50° C. for 1 hour, at 60° C. for 1 hour and at 90° C. for 3 hours.

After cooling the reaction mixture to room temperature, it was filtered and the filter cake was washed with acetone. The acetone used for washing and the above filtrate were mixed and the mixture was concentrated at a bath temperature of about 70° C. under a pressure of 30 mmHg to give 50 g of a concentrate.

To the obtained concentrate was added 250 ml of water, which was extracted three times with 50 ml of benzene and the obtained benzene layers were washed twice times with 100 ml of water. Benzene was distilled away from the solution to give 21.0 g of a light brown liquid.

As a result of the quantitative analysis of the liquid by gas chromatography, it was confirmed that the content of methyl 2,2-diallyl acetoacetate was 85% and its yield to methyl acetoacetate was 91% by mole.

Step (I) (1) (b)

An autoclave was charged with 21.0 g of the light brown liquid obtained in the step (I) (1) (a) and 0.84 g of Raney nickel (water content 50%) and catalytic hydrogenation was conducted in the same manner as in Example 1 and the obtained product was distilled under reduced pressure to give 18.4 g of a colorless liquid.

As a result of the analysis of the obtained liquid by gas chromatography, it was confirmed that the content of methyl 2,2-dipropyl acetoacetate was 95% and its yield to methyl acetoacetate was 96% by mole.

Step (II) and Step (III)

To 18.4 g of methyl 2,2-dipropyl acetoacetate were added 2.5 g of 28% methanol solution of sodium acetate and 3 g of methanol and the reaction was carried out according to Step (II) of Example 1 to give 15.9 g of a brown liquid.

To the obtained liquid were added 13 g of 40% aqueous solution of sodium hydroxide and 6 ml of water and valproic acid was prepared according to Step (III) of Example 1.

As a result of the analysis by gas chromatography, it was confirmed that the content of valproic acid was 95.7% and the yield of valproic acid to methyl acetoacetate was 85% by mole. Also α-propyl-β-ethyl acrylic acid and its esters were not entirely included in the obtained product.

What we claim is:

1. A process for producing valproic acid which comprises:
   (I) producing a 2,2-dipropyl acetoacetic acid ester from an acetoacetic acid ester by reacting said acetoacetic acid ester with an allyl halide to give a 2,2-diallyl acetoacetic acid ester in the presence of a basic catalyst or a basic catalyst and a phase-transfer catalyst and reducing said 2,2-diallyl acetoacetic acid ester or by reacting said acetoacetic acid ester with a propyl halide in the presence of a basic catalyst or a basic catalyst and a phase-transfer catalyst;
   (II) deacetylating said 2,2-dipropyl acetoacetic acid ester in the presence of a basic catalyst with an alcohol to give a valproic acid ester; and
   (III) hydrolyzing said valproic acid ester.

2. The process of claim 1, wherein said 2,2-diallyl acetoacetic acid ester is reduced by means of a catalytic hydrogenation.

3. The process of claim 2, wherein said catalytic hydrogenation is carried out in the presence of Raney nickel.

4. The process of claim 1, wherein said acetoacetic acid ester is reacted with said allyl halide in the presence of a basic catalyst and a phase-transfer catalyst.

5. The process of claim 4, wherein said phase-transfer catalyst is a quaternary ammonium salt.

6. A process of claim 1, wherein said acetoacetic acid ester is reacted with the allyl halide to give the 2,2-diallyl acetoacetic acid ester at a temperature of from 0° C. to a boiling point of a solvent or the allyl halide and in the presence of a basic catalyst and a phase-transfer catalyst and reduction of said 2,2-diallyl acetoacetic acid ester is effected at a temperature of from room temperature to 200° C.; or said 2,2-dipropyl acetoacetic acid ester is produced by reacting said acetoacetic acid ester with a propyl halide at a temperature of about 0° C. to about 90° C. in the presence of a basic catalyst and a phase-transfer catalyst and, thereafter, the 2,2-dipropyl acetoacetic acid ester is deacetylated with an alcohol at a temperature of from 50° C. to a reflux point in the presence of a basic catalyst.

7. A process for preparing valproic acid which comprises:
(I) producing a 2,2-dipropyl acetoacetic acid ester from an acetoacetic acid ester by reacting said acetoacetic acid ester with an allyl halide in the presence of a basic catalyst or a basic catalyst and a phase-transfer catalyst to give a 2,2-diallyl acetoacetic acid ester at a temperature of from 0° C. to a boiling point of the allyl halide and then reducing said 2,2-diallyl acetoacetic acid ester at a temperature from room temperature to 200° C. by catalytic hydrogenation;
(II) deacetylating said 2,2-dipropyl acetoacetic acid ester with an alcohol at a temperature from 50° C. to a reflex point to give a valproic acid ester in the presence of a basic catalyst; and
(III) hydrolyzing said valproic acid ester by heating under reflux at a temperature of from 50° C. to 100° C.

8. The process of claim 7, wherein said acetoacetic acid ester is reacted with the allyl halide in the presence of a solvent at a temperature from 0° C. to a boiling point of the solvent.

9. A process for preparing valproic acid which comprises:
(I) producing a 2,2-dipropyl acetoacetic acid ester from an acetic acid ester by reacting said acetoacetic acid ester with a propyl halide at a temperature of from 0° C. to 90° C. in the presence of a basic catalyst;
(II) deacetylating said 2,2-dipropyl acetoacetic acid ester with an alcohol at a temperature of from 50° C. to a reflux point to give a valproic acid ester in the presence of a basic catalyst; and
(III) hydrolyzing said valproic acid ester by heating under reflux at a temperature of from 50° C. to 100° C.

* * * * *